United States Patent
Nakai

(10) Patent No.: US 10,076,305 B2
(45) Date of Patent: Sep. 18, 2018

(54) COMPOSITION FOR ULTRASONIC PROBE, AND SILICONE RESIN FOR ULTRASONIC PROBE

(71) Applicant: FUJIFILM Corporation, Tokyo (JP)

(72) Inventor: Yoshihiro Nakai, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 15 days.

(21) Appl. No.: 15/268,899

(22) Filed: Sep. 19, 2016

(65) Prior Publication Data

US 2017/0000455 A1 Jan. 5, 2017

Related U.S. Application Data

(63) Continuation of application No. PCT/JP2015/053284, filed on Feb. 5, 2015.

(30) Foreign Application Priority Data

Mar. 27, 2014 (JP) ................................. 2014-066766

(51) Int. Cl.

| | | |
|---|---|---|
| *A61B 8/00* | (2006.01) | |
| *G10K 11/30* | (2006.01) | |
| *C08L 83/04* | (2006.01) | |
| *C08K 3/36* | (2006.01) | |
| *C08K 5/56* | (2006.01) | |
| *C08L 83/00* | (2006.01) | |
| *C08G 77/12* | (2006.01) | |
| *C08G 77/20* | (2006.01) | |

(52) U.S. Cl.
CPC .............. *A61B 8/4281* (2013.01); *C08K 3/36* (2013.01); *C08K 5/56* (2013.01); *C08L 83/00* (2013.01); *C08L 83/04* (2013.01); *G10K 11/30* (2013.01); *A61B 8/4444* (2013.01); *C08G 77/12* (2013.01); *C08G 77/20* (2013.01)

(58) Field of Classification Search
CPC ........... C08G 77/12; C08G 77/20; B01J 23/40
See application file for complete search history.

(56) References Cited

U.S. PATENT DOCUMENTS

| | | | | |
|---|---|---|---|---|
| 2011/0094403 A1* | 4/2011 | Verschuuren | ............ | B41N 1/12 101/450.1 |
| 2013/0266339 A1* | 10/2013 | Sugiyama | ................ | G03G 9/16 492/18 |

FOREIGN PATENT DOCUMENTS

| | | | |
|---|---|---|---|
| JP | 08-305375 A | | 11/1996 |
| JP | 2013122517 | * | 6/2013 |
| JP | 2013-199513 A | | 10/2013 |

OTHER PUBLICATIONS

Freeman (Silicones, Published for the Plastics Institute, Iliffe Books Ltd, 1962, p. 46) (Year: 1962).*
Communication dated Feb. 23, 2017, from the European Patent Office in counterpart European Application No. 15768250.1.
International Preliminary Report on Patentability dated Sep. 27, 2016, in corresponding International Application No. PCT/JP2015/053284 with English translation of Written Opinion, 12 pages in English and Japanese.
International Search Report of PCT/JP2015/053284 dated May 12, 2015.
Written Opinion of PCT/JP2015/053284 dated May 12, 2015.
Office Action of Corresponding Japanese Application No. 2014-066766 dated Jun. 28, 2016.

* cited by examiner

*Primary Examiner* — Kuo Liang Peng
(74) *Attorney, Agent, or Firm* — Sughrue Mion, PLLC

(57) ABSTRACT

A composition for an ultrasonic probe contains: a mixture including at least three different polyorganosiloxanes, in which the mixture includes (A) a polyorganosiloxane having a vinyl group, (B) a polyorganosiloxane having two or more Si—H groups in a molecular chain, and (C) a branched polyorganosiloxane represented by the following General Formula (C), and the content of the polyorganosiloxanes (A), (B), and (C) is respectively 10 to 99.4 parts by mass, 0.5 to 90 parts by mass, and 0.1 to 40 parts by mass, with respect to 100 parts by mass of the total mass of the polyorganosiloxanes mixture. R1 to R4 each independently represent an alkyl group, a cycloalkyl group, an alkenyl group, or an aryl group. m represents an integer of 1 or more and n represents 0 or an integer of 1 to 5. At least two of a plurality of R4's are alkenyl groups.

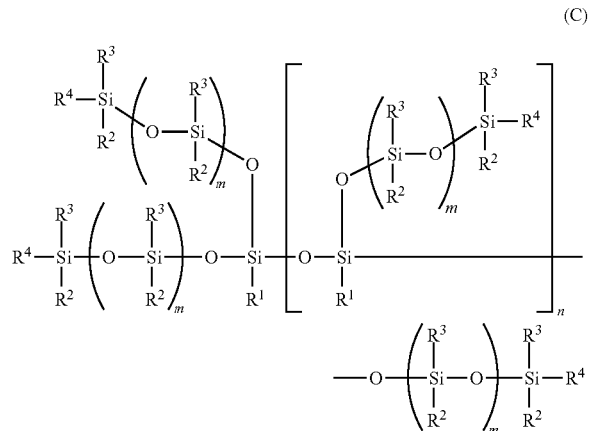

10 Claims, No Drawings

COMPOSITION FOR ULTRASONIC PROBE, AND SILICONE RESIN FOR ULTRASONIC PROBE

CROSS-REFERENCE TO RELATED APPLICATIONS

This application is a Continuation of PCT International Application No. PCT/JP2015/053284 filed on Feb. 5, 2015, which claims priority under 35 U.S.C § 119(a) to Japanese Patent Application No. 2014-066766 filed on Mar. 27, 2014. Each of the above application(s) is hereby expressly incorporated by reference, in its entirety, into the present application.

BACKGROUND OF THE INVENTION

1. Field of the Invention

The present invention relates to a composition for an ultrasonic probe and a silicone resin for an ultrasonic probe.

2. Description of the Related Art

A probe for ultrasound diagnostic apparatus (also referred to as an ultrasonic probe) includes a piezoelectric element transmitting/receiving ultrasonic waves, and an acoustic lens which is a portion brought into contact with a living body. Ultrasonic waves generated from the piezoelectric element are incident on a living body by being transmitted through the acoustic lens. If the difference between acoustic impedance (density×acoustic velocity) of acoustic lens and acoustic impedance of a living body is large, ultrasonic waves are reflected on the surface of the living body. Therefore, the ultrasonic waves are not effectively incident in a living body, and thus, it is difficult to obtain high resolution. For this reason, it is necessary to reduce ultrasonic attenuation by matching the acoustic impedance of the acoustic lens and the acoustic impedance of the living body.

Accordingly, a silicone resin which is close to acoustic impedance (1.4 to $1.7 \times 10^6$ kg/m²·sec) of a living body and of which ultrasonic attenuation is small has been mainly used as the material of the acoustic lens.

For example, in JP1996-305375A (JP-H8-305375A), a composition, which is formed of a silicone compound having a diorganopolysiloxane as a main agent and another kind of an organopolysiloxane, is proposed as a composition for an acoustic lens. There is a disclosure that, with use of this composition, it is possible to bring the acoustic impedance to a living body and to form an acoustic lens of which ultrasonic attenuation is small in a high frequency region and which has high resolution.

In addition, in JP2013-199513A, a composition containing a vinyl group-containing linear organopolysiloxane, a linear organohydrogenpolysiloxane, a specific vinyl group-containing branched organopolysiloxane, and an inorganic filling material is proposed as a silicone resin composition.

There is a disclosure that it is possible to obtain a silicone rubber member capable of withstanding large deformation by cross-linking a vinyl group and a Si—H group through a hydrosilylation reaction and making the molecular weight large.

SUMMARY OF THE INVENTION

The acoustic lens is made to abut on a subject, and therefore, mechanical strength for withstanding deformation during long-term usage is required. The silicone resin alone is soft and has low mechanical strength. Therefore, formulating of inorganic filler (also referred to as an inorganic filling material), such as silica, or a vinyl group-containing resin (also referred to as a reinforcing material) is performed while making the molecular weight of the silicone resin large, for the purpose of improving the hardness and the mechanical strength. In contrast, if the component constituting the acoustic lens material is a silicone resin alone, the ultrasonic attenuation is small. However, if inorganic filler or a vinyl group-containing resin is added to the silicone resin, there is a problem in that the ultrasonic attenuation is reversely increased.

In addition, in a case of using molecular chain-both terminal vinyl silicone having high molecular weight in order to improve the mechanical strength, there is a problem in that the number of cross-linking points necessarily decreases and the hardness decreases. In this manner, it cannot be said that the silicone resin so far satisfies both of the high resin hardness and mechanical strength, and low ultrasonic attenuation at a high level.

Accordingly, an object of the present invention is to provide a composition for an ultrasonic probe and a silicone resin for an ultrasonic probe which can improve the hardness and the mechanical strength of an obtained resin while maintaining low ultrasonic attenuation, in consideration of the above-described circumstances.

The present inventors have studied a composition in which various kinds of polyorganosiloxanes are contained. As a result, they have found that it is possible to solve the above-described problems in a specific compound.

The above-described problems have been solved through the following means.

<1> A composition for an ultrasonic probe which contains a polyorganosiloxane mixture including at least three different polyorganosiloxanes, in which (A) the polyorganosiloxane mixture includes a polyorganosiloxane having a vinyl group, (B) a polyorganosiloxane having two or more Si—H groups in a molecular chain, and (C) a branched polyorganosiloxane represented by the following General Formula (C), and the content of the polyorganosiloxanes (A), (B), and (C) is respectively 10 to 99.4 parts by mass, 0.5 to 90 parts by mass, and 0.1 to 40 parts by mass, with respect to 100 parts by mass of the total mass of the polyorganosiloxanes (A), (B), and (C).

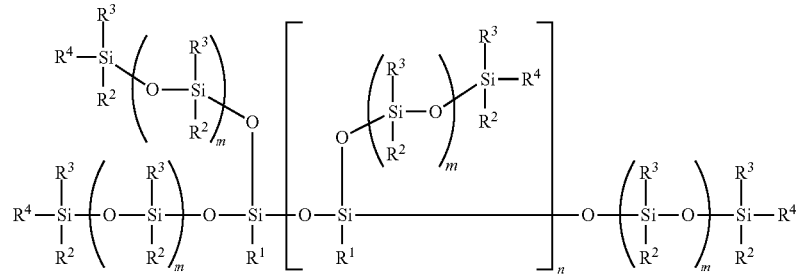

(C)

In General Formula (C), $R^1$ to $R^4$ each independently represent an alkyl group, a cycloalkyl group, an alkenyl group, or an aryl group. m represents an integer of 1 or more and n represents 0 or an integer of 1 to 5. A plurality of $R^1$'s, a plurality of $R^2$'s, a plurality of $R^3$'s, a plurality of $R^4$'s, and a plurality of m's may be the same as or different from each other, each group of $R^1$ to $R^4$ may be further substituted with a substituent. At least two of the plurality of $R^4$'s are alkenyl groups.

<2> The composition for an ultrasonic probe according to <1>, in which (C) the branched polyorganosiloxane represented by General Formula (C) is a branched polyorganosiloxane represented by the following General Formula (C1).

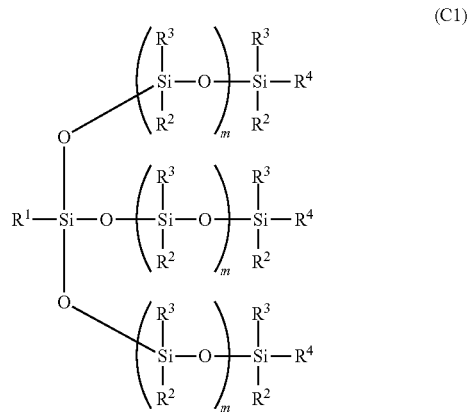

In General Formula (C1), $R^1$ to $R^4$ each independently represent an alkyl group, a cycloalkyl group, an alkenyl group, or an aryl group. m represents an integer of 1 or more. A plurality of $R^2$'s, a plurality of $R^3$'s, a plurality of $R^4$'s, and a plurality of m's may be the same as or different from each other, each group of $R^1$ to $R^4$ may be further substituted with a substituent. At least two of three $R^4$'s are alkenyl groups.

<3> The composition for an ultrasonic probe according to <1> or <2>, in which $R^1$ to $R^3$ are alkyl groups having 1 to 4 carbon atoms, $R^4$ is an alkyl group having 1 to 4 carbon atoms or a vinyl group, and at least two of the plurality of $R^4$'s are vinyl groups.

<4> The composition for an ultrasonic probe according to any one of <1> to <3>, in which $R^1$ to $R^3$ are methyl groups and $R^4$ is a vinyl group.

<5> The composition for an ultrasonic probe according to any one of <1> to <4>, in which (A) the polyorganosiloxane having a vinyl group is a polyorganosiloxane represented by the following General Formula (A).

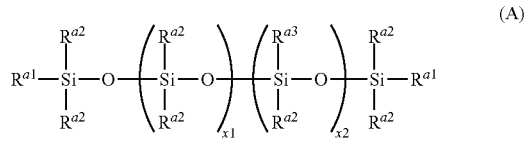

In General Formula (A), $R^{a1}$ represents a vinyl group, and $R^{a2}$ and $R^{a3}$ each independently represent an alkyl group, a cycloalkyl group, an alkenyl group, or an aryl group. x1 and x2 each independently represent an integer of 1 or more. A plurality of $R^{a2}$'s and a plurality of $R^{a3}$'s may be the same as or different from each other, each group of $R^{a2}$ and $R^{a3}$ may be further substituted with a substituent.

<6> The composition for an ultrasonic probe according to any one of <1> to <5>, in which (B) the polyorganosiloxane having two or more Si—H groups in a molecular chain is a polyorganosiloxane represented by the following General Formula (B)

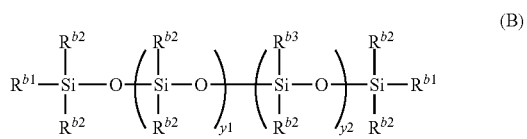

In General Formula (B), $R^{b1}$ to $R^{b3}$ each independently represent a hydrogen atom, an alkyl group, a cycloalkyl group, an alkenyl group, an aryl group, or —O—Si($R^{b5}$)$_2$ ($R^{b4}$)$_2R^{b4}$ and $R^{b5}$ each independently represent a hydrogen atom, an alkyl group, a cycloalkyl group, an alkenyl group, or an aryl group. y1 and y2 each independently represent an integer of 1 or more. A plurality of $R^{b1}$'s, a plurality of $R^{b2}$s, a plurality of $R^{b3}$'s, a plurality of $R^{b4}$'s, and a plurality of $R^{b5}$'s may be the same as or different from each other, each group of $R^{b1}$ to $R^{b5}$ may be further substituted with a substituent. The polyorganosiloxane has two or more Si—H groups in a molecular chain.

<7> The composition for an ultrasonic probe according to any one of <1> to <6>, further contains an inorganic filler, in which the content of the inorganic filler with respect to 100 parts by mass of the polyorganosiloxane mixture is 5 to 200 parts by mass.

<8> The composition for an ultrasonic probe according to any one of <1> to <7>, in which the (A) polyorganosiloxane having a vinyl group includes at least a vinyl group-containing silicone resin, and the content of the vinyl group-containing silicone resin with respect to 100 parts by mass of the total mass of the (A) component is 5 to 100 parts by mass.

<9> The composition for an ultrasonic probe according to any one of <1> to <8>, further contains a platinum or a platinum compound, in which the content of the platinum or the platinum compound with respect to 100 parts by mass of the polyorganosiloxane mixture is 0.01 to 5 parts by mass.

<10> A silicone resin for an ultrasonic probe which is obtained by curing the composition for an ultrasonic probe according to any one <1> to <9>.

In each general formula of the present specification, in a case where there are a plurality of groups having the same reference numerals, these groups may be the same as or different from each other, or a group (for example, an alkyl group or the like) specified by each group may be further substituted with a substituent, unless otherwise specified.

In addition, the meaning of "to" in the present specification includes numerical values denoted before and after "to" as a lower limit value and an upper limit value.

According to the present invention, it is possible to provide a composition for an ultrasonic probe and a silicone resin for an ultrasonic probe in which it is possible to obtain high resin hardness and mechanical strength without increasing ultrasonic attenuation.

It is inferred that the reason why it is possible to realize such an effect is as follows.

Cross-linking can be multi-dimensionally performed using a specific branched polyorganosiloxane having a polymerizable unsaturated group at a position at which cross-linking can be multi-dimensionally performed in three or more dimensions in a suitable space in addition to performing two-dimensional polymerization between a polyorganosiloxane, which has a hydrogen atom on a Si atom (silicon atom) and can perform hydrosilylation on a polymerizable unsaturated group, and a linear polyorganosiloxane having a polymerizable unsaturated group at terminal. Therefore, it is inferred that it is possible to improve the resin hardness and the mechanical strength while maintaining originally low ultrasonic attenuation of the silicone resin.

DESCRIPTION OF THE PREFERRED EMBODIMENTS

A composition for an ultrasonic probe of the present invention (hereinafter, also simply referred to as a "composition") contains a polyorganosiloxane mixture including at least three different polyorganosiloxanes, in which the polyorganosiloxane mixture includes (A) a polyorganosiloxane having a vinyl group (hereinafter, also referred to as an "(A) component"), (B) a polyorganosiloxane having two or more Si—H groups in a molecular chain (hereinafter, also referred to as a "(B) component"), and (C) a branched polyorganosiloxane represented by the following General Formula (C) (hereinafter, also referred to as a "(C) component"), and each of the content of the polyorganosiloxanes (A), (B), and (C) is respectively 10 to 99.4 parts by mass, 0.5 to 90 parts by mass, and 0.1 to 40 parts by mass, with respect to 100 parts by mass of the total mass of the polyorganosiloxanes (A), (B), and (C).

That is, the total mass of the (A) component, the (B) component, and the (C) component is 100 parts by mass.

The (A) component, the (B) component, and the (C) component are components different from each other, and the (A) component does not contain a branched polyorganosiloxane represented by General Formula (C) of the (C) component.

The polyorganosiloxane having a vinyl group of the (A) component is preferably 50 to 99 parts by mass and more preferably 70 to 95 parts by mass. The polyorganosiloxane having two or more Si—H groups in a molecular chain of the (B) component is preferably 0.5 to 20 parts by mass and more preferably 0.5 to 10 parts by mass. In contrast, the branched polyorganosiloxane represented by General Formula (C) of the (C) component is preferably 3 to 20 parts by mass and more preferably 5 to 15 parts by mass.

Hereinafter, the polyorganosiloxanes of the (A) component to the (C) component will be described in order.

<(A) Polyorganosiloxane Having Vinyl Group>

The polyorganosiloxane of the (A) component has a vinyl group, and preferably has (a) the vinyl group at least at both terminals of a molecular chain or has (b) at least two units of —O—Si(CH$_3$)$_2$(CH═CH$_2$) even if the position at which the polyorganosiloxane of the (A) component has —O—Si(CH$_3$)$_2$(CH═CH$_2$) is not both the terminals of a molecular chain. The polyorganosiloxane in (a) preferably has a linear shape. A case where —O—Si(CH$_3$)$_2$(CH═CH$_2$) in (b) is bonded to a Si atom constituting a main chain is preferable.

In the polyorganosiloxane having a vinyl group of the (A) component, at least two-dimensional cross-linking can be performed using (a) the vinyl group of both the terminals of a molecular chain or (b) the vinyl group of —O—Si(CH$_3$)$_2$(CH═CH$_2$) which is subjected to hydrosilylation with the polyorganosiloxane having two or more Si—H groups and a platinum catalyst and is subjected to addition cure.

The content of the vinyl group of the polyorganosiloxane of the (A) component is not particularly limited, but is, for example, 0.01 to 15 mol % and preferably 0.05 to 12 mol % from the viewpoint of forming a sufficient network with each component contained in the composition.

Here, the content of the vinyl group indicates mol % of a vinyl group-containing siloxane unit when all units constituting the polyorganosiloxane is set to 100 mol %, and it is regarded such that there is a vinyl group with respect to a vinyl group-containing siloxane unit.

The unit refers to a Si—O unit and Si at a terminal, which constitute a main chain.

The degree of polymerization and the specific gravity are not particularly limited. However, the degree of polymerization is preferably 3000 to 10000 and more preferably 4000 to 8000, and the specific gravity is preferably 0.9 to 1.1 from the viewpoint of improving mechanical characteristics, the hardness, the chemical stability, or the like of a silicone resin to be obtained.

The weight-average molecular weight is not particularly limited, but is preferably less than or equal to 500,000, more preferably less than or equal to 400,000, and still more preferably 200,000 to 350,000. The weight-average molecular weight can be measured (in terms of polystyrene) using gel permeation chromatography (GPC).

The kinematic viscosity at 25° C. is preferably 1×10$^{-7}$ to 10 m$^2$/s, more preferably 1×10$^{-4}$ to 1 m$^2$/s, and still more preferably 1×10$^{-3}$ to 0.5 m$^2$/s.

The polyorganosiloxane of the (A) component is preferably a polyorganosiloxane having (a) a vinyl group at least at both terminals of a molecular chain and more preferably a polyorganosiloxane represented by the following General Formula (A).

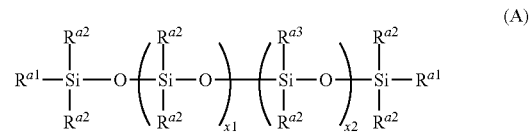

(A)

In General Formula (A), R$^{a1}$ represents a vinyl group, and R$^{a2}$ and R$^{a3}$ each independently represent an alkyl group, a cycloalkyl group, an alkenyl group, or an aryl group. x1 and x2 each independently represent an integer of 1 or more. Here, a plurality of R$^{a2}$'s and a plurality of R$^{a3}$'s may be the same as or different from each other or each group of R$^{a2}$ and R$^{a3}$ may be further substituted with a substituent.

The number of carbon atoms of the alkyl group in R$^{a2}$ and R$^{a3}$ is preferably 1 to 10, more preferably 1 to 4, and still more preferably 1. Examples of the alkyl group include a methyl group, an ethyl group, an n-propyl group, an isopropyl group, an n-butyl group, an isobutyl group, an n-hexyl group, an n-octyl group, a 2-ethylhexyl group, and an n-decyl group.

The number of carbon atoms of the cycloalkyl group in R$^{a2}$ and R$^{a3}$ is preferably 3 to 10, more preferably 5 to 10, and still more preferably 5 or 6. In addition, the cycloalkyl group is preferably a 3-membered ring, a 5-membered ring, or a 6-membered ring, or is more preferably a 5-membered ring or a 6-membered ring. Examples of the cycloalkyl group include a cyclopropyl group, a cyclopentyl group, and a cyclohexyl group.

The number of carbon atoms of the alkenyl group in R$^{a2}$ and R$^{a3}$ is preferably 2 to 10, more preferably 2 to 4, and still more preferably 2, and examples thereof include a vinyl group, an allyl group, and a butenyl group.

The number of carbon atoms of the aryl group in R and R$^{a3}$ is preferably 6 to 12, more preferably 6 to 10, and still more preferably 6 to 8, and examples thereof include a phenyl group, a tolyl group, and a naphthyl group.

These alkyl groups, cycloalkyl groups, alkenyl groups, and aryl groups, may have a substituent. Examples thereof include a halogen atom, an alkyl group, a cycloalkyl groups, an alkenyl group, an aryl group, an alkoxy group, an aryloxy group, an alkylthio group, an arylthio group, a silyl group, and a cyano group.

$R^{a2}$ and $R^{a3}$ are preferably an alkyl group, an alkenyl group, or an aryl group, more preferably an alkyl group having 1 to 4 carbon atoms, a vinyl group, or a phenyl group, and still more preferably a methyl group or a vinyl group.

Among these, $R^{a2}$ is preferably a methyl group and $R^{a3}$ is preferably a methyl group or a vinyl group, and particularly preferably a vinyl group.

x1 is preferably an integer of 3000 to 10000 and more preferably an integer of 3600 to 8000.

x2 is preferably an integer of 1 to 1000 and more preferably an integer of 40 to 700.

In addition, the polyorganosiloxane of (b) is more preferably a polyorganosiloxane having a structure represented by the following General Formula (Ab).

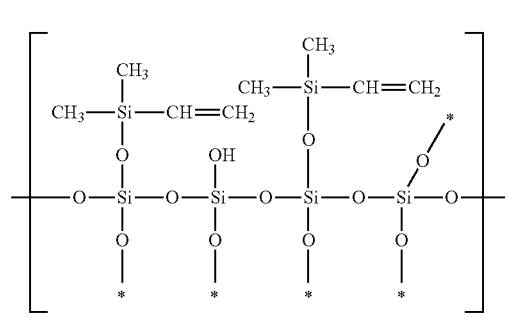

(Ab)

In General Formula (Ab), * means that the group is bonded to at least a Si atom of the siloxane.

Among the polyorganosiloxanes of the (A) component, examples of the polyorganosiloxane of (a) include a DMS series, such as DMS-V31, DMS-V31S15, DMS-V33, DMS-35, DMS-35R, DMS-V41, DMS-V42, DMS-V46, DMS-V51, and DMS-V52 which are trade names manufactured by GELEST, INC.; a PDV series, such as PDV-0341, PDV-0346, PDV-0535, PDV-0541, PDV-01631, PDV-01635, PDV-01641, and PDV-2335, which are trade names manufactured by GELEST, INC.; PMV-9925; PVV-3522; FMV-4031; and EDV-2022.

Among the polyorganosiloxane of the (A) component, the polyorganosiloxane of (b) also refers to a vinyl group-containing silicone resin, and is generally an addition cure elastomer which is used for improving the mechanical strength of the silicone resin and for increasing the hardness of the resin. The polyorganosiloxane of (b) is also preferably used in the present invention. A commercially available resin can be obtained as such a vinyl group-containing silicone resin. Examples thereof include a vinyl group-containing vinyl Q resin dispersion liquid (trade names: "VQM-135" (of which a base is DMS-V41), "VQM-146" (of which a base is DMS-V46), or "VQX-221" (of which a base is xylene), all are manufactured by GELEST, INC.) which is obtained by dispersing a vinyl group-containing polysiloxane (Q resin) having a Q unit in a dispersion liquid. The Q unit refers that no organic group is bonded to the Si atom in siloxane bond.

The polyorganosiloxane of the (A) component may be singly used or two or more kinds thereof may be used in combination. Alternately, the polyorganosiloxane of (a) and the polyorganosiloxane of (b) may be used in combination.

The amount of the vinyl group-containing silicone resin as the polyorganosiloxane of (b) is preferably 5 to 100 parts by mass, more preferably 6 to 70 parts by mass, and still more preferably 7 to 50 parts by mass with respect to 100 parts by mass of the total mass of the (A) component.

<(B) Polyorganosiloxane Having Two or More Si—H Groups in Molecular Chain>

The polyorganosiloxane of the (B) component has two or more Si—H groups in a molecular chain.

It is possible to perform cross-linking with a polyorganosiloxane having at least two polymerizable unsaturated groups since two or more Si—H groups are provided in a molecular chain.

In the polyorganosiloxane of the (B) component, there is a linear structure and a branched structure, and a linear structure is preferable.

The molecular weight of the linear structure is not particularly limited, but the weight-average molecular weight is preferably less than or equal to 20,000, more preferably 500 to 10,000, and still more preferably 800 to 7,000. The weight-average molecular weight can be measured (in terms of polystyrene) using gel permeation chromatography (GPC).

In addition, in a case where the number of Si atoms is set to 1, the number (R/Si) of alkyl groups R bonded to the Si atoms is preferably 1.8 to 2.1.

The linear polyorganosiloxane is preferably a polyorganosiloxane represented by the following General Formula (B).

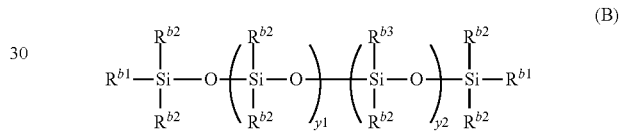

(B)

In General Formula (B), $R^{b1}$ to $R^{b3}$ each independently represent a hydrogen atom, an alkyl group, a cycloalkyl group, an alkenyl group, an aryl group, or $—O—Si(R^{b5})_2(R^{b4})_2$, $R^{b4}$ and $R^{b5}$ each independently represent a hydrogen atom, an alkyl group, a cycloalkyl group, an alkenyl group, or an aryl group. y1 and y2 each independently represent an integer of 1 or more. Here, a plurality of $R^{b1}$'s, a plurality of $R^{b2}$'s, a plurality of $R^{b3}$'s, a plurality of $R^{b4}$'s, and a plurality of $R^{b5}$'s independently may be the same as or different from each other or each group of $R^{b1}$ to $R^{b5}$ may be further substituted with a substituent. However, the polyorganosiloxane has two or more Si—H groups in a molecular chain.

The alkyl group, the cycloalkyl groups, the alkenyl group, and the aryl group in $R^{b1}$ to $R^{b3}$ are synonymous to those in $R^{a2}$ and $R^{a3}$, and the preferred ranges thereof are also the same as those in $R^{a2}$ and $R^{a3}$.

The alkyl group, the cycloalkyl groups, the alkenyl group, and the aryl group in $R^{b4}$ and $R^{b5}$ of $—O—Si(R^{b5})_2(R^{b4})$ are synonymous to those in $R^{b1}$ to $R^{b3}$, and the preferred ranges thereof are also the same as those in $R^{b1}$ to $R^{b3}$.

As $R^{b1}$ to $R^{b3}$, a hydrogen atom, an alkyl group, an alkenyl group, an aryl group, or $—O—Si(R^{b5})_2(R^{b4})$ is preferable and a hydrogen atom, an alkyl group having 1 to 4 carbon atoms, a vinyl group, a phenyl group, or $—O—Si(CH_3)_2H$ is more preferable.

Among these, as $R^{b1}$ and $R^{b2}$, a hydrogen atom, an alkyl group, an alkenyl group, or an aryl group is preferable, a hydrogen atom or an alkyl group is more preferable, and a hydrogen atom or a methyl group is particularly preferable.

As $R^{b3}$, a hydrogen atom, an alkyl group, an alkenyl group, an aryl group, or $—O—Si(R^{b5})_2(R^{b4})$ is preferable and a hydrogen atom, an alkyl group having 1 to 4 carbon atoms, an phenyl group, or $—O—Si(CH_3)_2H$ is more preferable.

As y1 and y2, an integer of 0 to 300 is preferable, an integer of 0 to 50 is more preferable, and an integer of 0 to 42 is still more preferable.

As y1+y2, an integer of 2 to 300 is preferable, an integer of 2 to 100 is more preferable, an integer of 5 to 50 are still more preferable, and an integer of 8 to 42 is particularly preferable.

The linear structure and the branched structure does not preferably have a vinyl group from the viewpoint of preventing progress of a crosslinking reaction in a molecular chain, and among these, a polyorganosiloxane with a branched structure does not preferably has a vinyl group.

The polyorganosiloxane with a branched structure (hereinafter, also simply referred to as a "branched shape") has a branched structure and a structure (Si—H) in which a hydrogen atom is directly bonded to a Si atom.

The specific gravity is preferably 0.9 to 0.95 and the number (R/Si) of alkyl groups R bonded to a Si atom in a case where the number of Si atoms is set to 1 is preferably 0.8 to 1.7.

The branched polyorganosiloxane is preferably a polyorganosiloxane represented by the following Average Composition Formula (b).

Average Composition Formula (b): $[H_a(R^{b6})_{3-a}SiO_{1/2}]_{y3}[SiO_{4/2}]_{y4}$ Here, $R^{b6}$ represents an alkyl group, a cycloalkyl group, an alkenyl group, or an aryl group, a represents an integer of 1 to 3, y3 and y4 are synonymous to those in y1 and y2, and the preferred ranges thereof are also the same as those in y1 and y2.

In contrast, when the branched polyorganosiloxane is represented by a chemical structural formula, a polyorganosiloxane in which —O—Si(CH$_3$)$_2$(H) is bonded to a Si atom constituting a main chain is preferable and a polyorganosiloxane having a structure represented by the following General Formula (Bb) is more preferable.

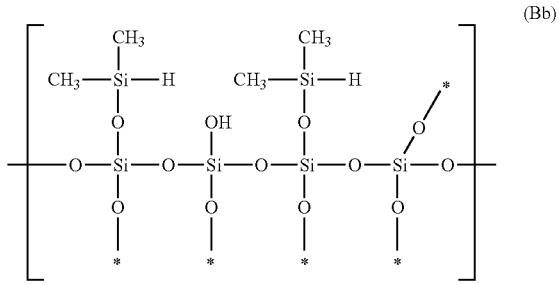
(Bb)

In General Formula (Bb), * means that the group is bonded to at least a Si atom of the siloxane.

Examples of the polyorganosiloxane of the (B) component with a linear structure include Linear ORGANOHYDROGENPOLYSILOXANE 88466 (trade names, manufactured by Momentive Performance Materials Inc, polydimethyl-co-methylhydride siloxane, y1=14, y2=11), HMS-082 (trade names, manufactured by GELEST, INC., MethylHydrosiloxane-(Dimethysiloxane Copolymers, Trimethylsiloxy terminated, weight-average molecular weight: 5500 to 6500, MeHSiO: 7 to 8 mol %, y1=39, y2=3), and HMS-501 (trade names, manufactured by GELEST, INC., MethylHydrosiloxane-(Dimethysiloxane Copolymers, Trimethylsiloxy terminated, weight-average molecular weight: 900 to 1,200, MeHSiO: 50 to 55 mol %, y1=4, y2=4).

Examples of the polyorganosiloxane having a branched structure include HQM-107 (trade names, manufactured by GELEST, INC., Hydrid Q Resin) and HDP-111 (trade names, manufactured by GELEST, INC., polyPhenyl-(DiMethylHydrosiloxy)siloxane, hydride terminated, [(HMe$_2$SiO)(C$_6$H$_3$Si)O]: 99 to 100 mol %).

(B) The polyorganosiloxane having two or more Si—H groups in a molecular chain may be used singly, or two or more kinds thereof may be used in combination. The polyorganosiloxane having a linear structure and the polyorganosiloxane having a branched structure may be used in combination.

<(C) Branched Polyorganosiloxane Represented by General Formula (C)>

In the polyorganosiloxane of the (C) component which contributes to exhibit the effect of the present invention, cross-linking can be multi-dimensionally performed in three or more dimensions. Unlike two-dimensional cross-linking in the related art or partially three-dimensional cross-linking in a narrow space, multi-dimensional cross-linking in three or more dimensions in which a suitable spatial distance is maintained can be performed, and plays an important role when solving the problems of the present invention.

The polyorganosiloxane of the (C) component in the present invention is represented by the following General Formula (C).

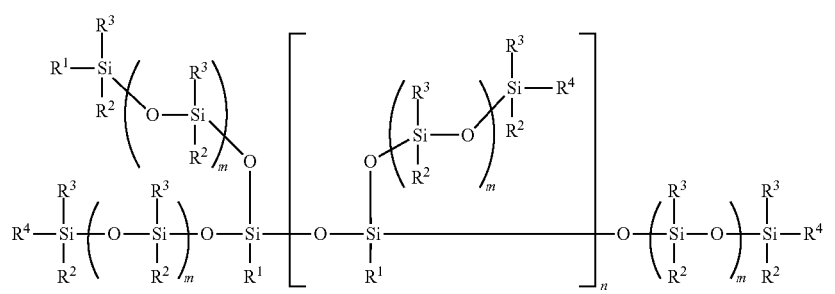
(C)

In General Formula (C), $R^1$ to $R^4$ each independently represent an alkyl group, a cycloalkyl group, an alkenyl group, or an aryl group. m represents an integer of 1 or more and n represents 0 or an integer of 1 to 5. Here, a plurality of $R^1$'s, a plurality of $R^2$'s, a plurality of $R^3$'s, a plurality of $R^4$'s, and a plurality of m's may be the same as or different from each other or each group of $R^1$ to $R^4$ may be further substituted with a substituent. However, at least two of the plurality of $R^4$'s are alkenyl groups.

In General Formula (C), n is preferably 0 and can be represented by the General Formula (C1).

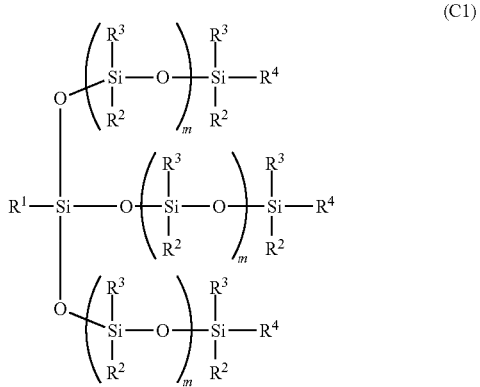

(C1)

In General Formula (C1), $R^1$ to $R^4$ each independently represent an alkyl group, a cycloalkyl group, an alkenyl group, or an aryl group. m represents an integer of 1 or more. Here, a plurality of $R^2$'s, a plurality of $R^3$'s, a plurality of $R^4$'s, and a plurality of m's may be the same as or different from each other or each group of $R^1$ to $R^4$ may be further substituted with a substituent. However, at least two of three $R^4$'s are alkenyl groups.

In General Formulas (C) and (C1), the above-described each group in $R^1$ to $R^4$ is synonymous to that in $R^{a2}$ and $R^{a3}$ in General Formula (A), the preferred ranges thereof are also the same as those in $R^{a2}$ and $R^{a3}$.

m is preferably 1 to 20, more preferably 1 to 10, and still more preferably 1 to 5.

The weight-average molecular weight is not particularly limited, but is preferably 300 to 5,000, more preferably 300 to 2,500, and still more preferably 500 to 1,500. The weight-average molecular weight can be measured (in terms of polystyrene) using gel permeation chromatography (GPC).

The kinematic viscosity is preferably $1 \times 10^{-6}$ to $1 \times 10^{-2}$ $m^2/s$, more preferably $1 \times 10^{-6}$ to $1 \times 10^{3}$ $m^2/s$, and still more preferably $1 \times 10^{-5}$ to $1 \times 10^{-4}$ $m^2/s$.

The content and the specific gravity of a polymerizable unsaturated group of the polyorganosiloxane of the (C) component are not particularly limited. However, the content of the polymerizable unsaturated group is, for example, 5 to 100 mol % and preferably 20 to 50 mol % in terms of a vinyl group and the specific gravity thereof is preferably 0.8 to 1.1, from the viewpoint of forming a sufficient network with each component contained in the composition.

Here, similarly to the case of the polyorganosiloxane of the (A) component, the content of a polymerizable unsaturated group in terms of a vinyl group indicates mol % of a polymerizable unsaturated group (in terms of a vinyl group)-containing siloxane unit when all units constituting the polyorganosiloxane is set to 100 mol %, and it is regarded such that there is a polymerizable unsaturated group (vinyl group) with respect to a polymerizable unsaturated group (in terms of a vinyl group)-containing siloxane unit.

Examples of the polyorganosiloxane of the (C) component include MTV-112 (trade name, manufactured by GELEST, INC.).

The polyorganosiloxane of the (C) component may be used singly, or two or more kinds thereof may be used in combination.

The composition for an ultrasonic probe of the present invention contains a polyorganosiloxane mixture consisting of at least three different kinds of polyorganosiloxanes, which are (A) the above-described polyorganosiloxane having a vinyl group, (B) the above-described polyorganosiloxane having two or more Si—H groups in a molecular chain, and (C) a branched polyorganosiloxane represented by General Formula (C). The (A) component, the (B) component, and the (C) component are respectively contained in a ratio of 10 to 99.4 parts by mass, 0.5 to 90 parts by mass, and 0.1 to 40 parts by mass, with respect to 100 parts by mass of the total mass of the polyorganosiloxanes (A), (B), and (C).

The preferred range of the parts by mass is as described above. However, more specifically, the (A) component is preferably 30 to 99.3 parts by mass, more preferably 40 to 99.2 parts by mass, still more preferably 50 to 99 parts by mass, and particularly preferably 70 to 95 parts by mass.

The (B) component is preferably 0.5 to 70 parts by mass, more preferably 0.5 to 60 parts by mass, still more preferably 0.5 to 50 parts by mass, particularly preferably 0.5 to 20 parts by mass, and most preferably 0.5 to 10 parts by mass.

In addition, the (C) component is preferably 0.5 to 30 parts by mass, more preferably 1 to 25 parts by mass, still more preferably 2 to 20 parts by mass, particularly preferably 3 to 20 parts by mass, and most preferably 5 to 15 parts by mass.

<Other Materials>

The composition of the present invention can further contain an inorganic filler, a platinum catalyst for causing an addition polymerization reaction, a solvent, a dispersing agent, a pigment, dye, an antistatic agent, an antioxidant, a flame retardant, a thermoconductive improver, or the like, in addition to the polyorganosiloxanes of the (A) to (C) components.

[Inorganic Filler]

Examples of the inorganic filler include iron oxide, zinc oxide, titanium oxide, barium oxide, magnesium oxide, cerium oxide, calcium carbonate, magnesium carbonate, zinc carbonate, and glass wool, while having silica particles such as diatomaceous earth or mica as representatives.

The content of the inorganic filler is preferably 5 to 200 parts by mass, more preferably 7 to 100 parts by mass, and still more preferably 10 to 80 parts by mass with respect to 100 parts by mass of the polyorganosiloxane mixture.

Among these, silica particles are preferable.

—Silica Particles—

Silica particles are components which are added for the purpose of improving the hardness or the mechanical strength of a silicone resin to be obtained, and particularly improving the tensile strength.

The silica particles are not particularly limited, and examples thereof include fumed silica, burned silica, precipitated silica, and a vinyl group-containing silicone resin. The silica particles may be used singly, or two or more kinds thereof may be used in combination.

The specific surface area of silica particles is preferably 50 $m^2/g$ to 400 $m^2/g$ and more preferably 100 $m^2/g$ to 400 $m^2/g$ from the viewpoint of improving the hardness or the mechanical strength of a silicone resin to be obtained. In addition, the average particle diameter of silica particles is preferably 1 nm to 100 nm and more preferably 5 nm to 20 nm from the same viewpoint.

The inorganic filler is preferably inorganic filler which is obtained by subjecting the surface of particles to surface treatment. As the surface treatment, inorganic filler which is treated with saturated fatty acid or silane is preferable and inorganic filler which is subjected to silane treatment is particularly preferable.

As the silane treatment, treatment of the surface of particles is preferably performed using a silane coupling agent. A silicone resin preferably has a hydrolyzable group from the viewpoint of improving the hardness or the mechanical strength of the silicone resin. Surface modification of silica particles is performed such that this hydrolyzable group is hydrolyzed using water to become a hydroxyl group which is subjected to a dehydration condensation reaction with a hydroxyl group of the surface of inorganic filler such as silica particles. Accordingly, the hardness or the mechanical strength of the thus obtained silicone resin is improved.

Examples of the silane coupling agent having a hydrophobic group as a functional group include alkoxysilane such as methyltrimethoxysilane, dimethyldimethoxysilane, phenyltrimethoxysilane, methyltriethoxysilane, dimethyldiethoxysilane, phenyltriethoxysilane, n-propyltrimethoxysilane, n-propyltriethoxysilane, hexyltrimethoxysilane, hexyltriethoxysilane, and decyltrimethoxysilane; chlorosilane such as methyltrichlorosilane, dimethyldichlorosilane, trimethylchlorosilane, and phenyltrichlorosilane; and hexamethyldisilazane. Examples of the silane coupling agent having a vinyl group as a functional group include alkoxysilane such as methacryloxypropyltriethoxysilane, methacryloxypropyltrimethoxysilane, methacryloxypropylmethyldiethoxysilane, methacryloxypropylmethyldimethoxysilane, vinyl triethoxysilane, vinyltrimethoxysilane, and vinylmethyldimethoxysilane; chlorosilane such as vinyltrichlorosilane and vinylmethyldichlorosilane; and divinyltetramethyldisilazane. Among these, when considering the above description, specific examples of the silane coupling agent having a hydrophobic group include hexamethyldisilazane, and specific examples of the silane coupling agent having a vinyl group include divinyltetramethyldisilazane.

Examples of a commercially available silane coupling agent include hexamethyldisilazane (HMDZ) (trade name: HEXAMETHYLDISILAZANE (SIH6110.1) manufactured by GELEST, INC.).

Examples of commercially available silica particles include fumed silica (manufactured by NIPPON AEROSIL CO., LTD., "AEROSIL R974"), silica dioxide (trade name: AEROSIL200, manufactured by NIPPON AEROSIL CO., LTD., Surface preparation: —Si(CH$_3$)(—CH=CH$_2$ optional), Filter specific surface: 200 m$^2$/g).

The content of inorganic filler is preferably 5 to 200 parts by mass and more preferably 10 to 40 parts by mass with respect to 100 parts by mass of the total solid content mass of a composition from the viewpoint of improving dispersibility in the composition. Accordingly, inorganic filler can reliably improve dispersibility in the composition.

—Catalyst—

Examples of the catalyst include a platinum or a platinum compound. A well-known platinum or platinum compound can be used. Specific examples thereof include platinum black; platinum supported on silica, carbon black, or the like; chloroplatinic acid or an alcohol solution of chloroplatinic acid; complex salts of chloroplatinic acid and olefins, and complex salts of chloroplatinic acid and vinylsiloxane. The catalyst may be used singly, or two or more thereof may be used in combination.

The content of the catalyst can be appropriately set within a range of the amount of catalyst.

The catalyst is required for hydrosilylation reaction in which a Si—H group of the polyorganosiloxane of the (B) component is added to a polymerizable unsaturated group of the polyorganosiloxane of the (A) component or the (C) component. A silicone resin is formed through polymerization performed by hydrosilylation.

Here, the catalyst may be contained in the composition or may be brought into contact with the composition without being contained in the composition. However, the latter case is preferable.

Examples of the platinum catalyst include a platinum compound (trade name: PLATINUM DIVINYLTETRAMETHYLDISILOXANE COMPLEX in xylene (SIP6831.2), manufactured by GELEST, INC.).

In a case where a catalyst is contained in the composition, the content of the catalyst is preferably 0.01 to 5 parts by mass, more preferably 0.001 to 1 part by mass, and still more preferably 0.005 to 0.1 parts by mass with respect to 100 parts by mass of the polyorganosiloxane mixture from the viewpoint of reactivity.

<Method for Preparing Composition for Ultrasonic Probe and Silicone Resin for Ultrasonic Probe>

The composition for an ultrasonic probe of the present invention can be prepared through a well-known method. For example, the composition can be obtained by kneading the above-described component using a kneader, a pressurizing kneader, a Banbury mixer (continuous kneader), and a two-roll kneading device. The order of mixing each component is not particularly limited. However, from the viewpoint of obtaining a homogeneous composition, it is preferable to first disperse inorganic filler in (A) the polyorganosiloxane having a vinyl group, (B) the polyorganosiloxane having two or more Si—H groups in a molecular chain, and (C) the branched polyorganosiloxane represented by General Formula (C). Thereafter, it is possible to prepare a composition for an ultrasonic probe by adding a catalyst to this mixture to perform defoaming under reduced pressure.

It is possible to obtain a silicone resin for an ultrasonic probe by heating and curing the composition for an ultrasonic probe of the present invention which has been obtained as described above at, for example, 20 to 50° C. for 5 minutes to 500 minutes.

<Ultrasonic Probe>

The composition for an ultrasonic probe of the present invention is useful for a medical member. Particularly, the composition can be favorably used in a material or the like of an acoustic matching layer which plays a role of matching acoustic impedance between a piezoelectric element and an acoustic lens by being provided in the acoustic lens of the ultrasound diagnostic apparatus or between the piezoelectric element and the acoustic lens. The silicone resin for an ultrasonic probe of the present invention can be preferably applied to, for example, photoacoustic measurement devices disclosed in JP2013-202050A, JP2013-188465A, JP2013-180330A, JP2013-158435A, JP2013-154139A, and the like, or to ultrasound diagnostic apparatuses disclosed in JP2005-253751A, JP2003-169802A, and the like.

EXAMPLES

The present invention will be more specifically described based on Examples below, but is not interpreted to be limited thereto.

Example 1

88 parts by mass of a vinyl-terminated polydimethylsiloxane (kinematic viscosity of 0.1 m$^2$/s, manufactured by GELEST, INC., "DMS-V51"), 2 parts by mass of a methylhydrosiloxane-dimethylsiloxane copolymer (molecular weight of 2,000, methylhydrosiloxane proportion of 27 mol %, manufactured by GELEST, INC., "HMS-301"), 10 parts by mass of a branched vinyl-terminated branched polydimethylsiloxane (manufactured by GELEST, INC., "MTV-112"), and 20 parts by mass of fumed silica (manufactured by NIPPON AEROSIL CO., LTD., "AEROSIL R974") were kneaded for 2 hours using a kneader to make homogeneous paste. 500 ppm of a platinum catalyst solution (manufactured by GELEST, INC., "SIP6821.3") was added to and mixed with the paste. The mixed paste was defoamed under reduced pressure and was placed in a 150 mm×150 mm metal mold. Heat treatment was performed thereon for 15 minutes at 150° C. to obtain resin sheets each having a thickness of 1 mm, 2 mm, and 3 mm.

Example 2

83 parts by mass of a vinyl-terminated polydimethylsiloxane (manufactured by GELEST, INC., "VQM-146") which contains 23 mass % of a vinyl group-containing silicone resin, 7 parts by mass of a methylhydrosiloxane-dimethylsiloxane copolymer (molecular weight of 2,000, methylhydrosiloxane proportion of 27 mol %, manufactured by GELEST, INC., "HMS-301"), 10 parts by mass of a branched vinyl-terminated branched polydimethylsiloxane (manufactured by GELEST, INC., "MTV-112"), and 5 parts by mass of fumed silica (manufactured by NIPPON AEROSIL CO., LTD., "AEROSIL R974") were mixed with each other in the same manner as in Example 1, and the mixture was thermally cured using the same platinum catalyst solution as that in Example 1 to obtain a predetermined resin sheet.

Example 3

89 parts by mass of a vinyl-terminated polydimethylsiloxane (kinematic viscosity of 0.165 $m^2/s$, manufactured by GELEST, INC., "DMS-V52"), 1 part by mass of a methylhydrosiloxane-dimethylsiloxane copolymer (molecular weight of 1,000, methylhydrosiloxane proportion of 53 mol %, manufactured by GELEST, INC., "HMS-501"), 10 parts by mass of a branched vinyl-terminated branched polydimethylsiloxane (manufactured by GELEST, INC., "MTV-112"), and 20 parts by mass of fumed silica (manufactured by NIPPON AEROSIL CO., LTD., "AEROSIL R974") were mixed with each other in the same manner as in Example 1, and the mixture was thermally cured using the same platinum catalyst solution as that in Example 1 to obtain a predetermined resin sheet.

Comparative Example 1

98 parts by mass of a vinyl-terminated polydimethylsiloxane (kinematic viscosity of 0.1 $m^2/s$, manufactured by GELEST, INC., "DMS-V51"), 2 parts by mass of a methylhydrosiloxane-dimethylsiloxane copolymer (molecular weight of 2,000, methylhydrosiloxane proportion of 27 mol %, manufactured by GELEST, INC., "HMS-301"), and 20 parts by mass of fumed silica (manufactured by NIPPON AEROSIL CO., LTD., "AEROSIL R974") were mixed with each other in the same manner as in Example 1, and the mixture was thermally cured using the same platinum catalyst solution as that in Example 1 to obtain a predetermined resin sheet.

Comparative Example 2

98 parts by mass of a vinyl-terminated polydimethylsiloxane (kinematic viscosity of 0.1 $m^2/s$, manufactured by GELEST, INC., "DMS-V51") and 2 parts by mass of a methylhydrosiloxane-dimethylsiloxane copolymer (molecular weight of 2,000, methylhydrosiloxane proportion of 27 mol %, manufactured by GELEST, INC., "HMS-301") were mixed with each other in the same manner as in Example 1, and the mixture was thermally cured using the same platinum catalyst solution as that in Example 1 to obtain a predetermined resin sheet.

Comparative Example 3

98 parts by mass of a vinyl-terminated polydimethylsiloxane (kinematic viscosity of 0.1 $m^2/s$, manufactured by GELEST, INC., "DMS-V51"), 2 parts by mass of a methylhydrosiloxane-dimethylsiloxane copolymer (molecular weight of 2,000, methylhydrosiloxane proportion of 27 mol %, manufactured by GELEST, INC., "HMS-301"), and 34 parts by mass of fumed silica (manufactured by NIPPON AEROSIL CO., LTD., "AEROSIL R974") were mixed with each other in the same manner as in Example 1, and the mixture was thermally cured using the same platinum catalyst solution as that in Example 1 to obtain a predetermined resin sheet.

Comparative Example 4

78 parts by mass of a vinyl-terminated polydimethylsiloxane (kinematic viscosity of 0.1 $m^2/s$, manufactured by GELEST, INC., "DMS-V51"), 20 parts by mass of a vinyl group-containing linear polydimethylsiloxane prepared through a method disclosed in paragraph 0052 of JP2013-199513A, 2 parts by mass of a methylhydrosiloxane-dimethylsiloxane copolymer (molecular weight of 2,000, methylhydrosiloxane proportion of 27 mol %, manufactured by GELEST, INC., "HMS-301"), and 20 parts by mass of fumed silica (manufactured by NIPPON AEROSIL CO., LTD., "AEROSIL R974") were mixed with each other in the same manner as in Example 1, and the mixture was thermally cured using the same platinum catalyst solution as that in Example 1 to obtain a predetermined resin sheet.

<Evaluation of Mechanical Strength and Ultrasonic Characteristics>

The following evaluation was performed on silicone resins in Examples 1 to 3 and Comparative Examples 1 to 4. The results are shown in the following Table 1.

(Hardness)

The type-A durometer hardness of the obtained each sheet having a thickness of 3 mm was measured using a rubber hardness meter (manufactured by Excel Co., Ltd., "RH-201A") in accordance with JIS K6253-3 (2007).

(Tensile Strength Test)

The rupture strength and the elongation of the obtained each sheet having a thickness of 1 mm was measured in accordance with JIS K6251 (2010).

(Tear Strength Test)

A trousers-type specimen for the obtained each sheet having a thickness of 2 mm was produced to measure the tear strength thereof in accordance with JIS K 6252 (2007).

(Acoustic Impedance)

The density of the obtained each sheet having a thickness of 3 mm at 25° C. was obtained in accordance with JIS C-2123 (1993), the acoustic velocity at 25° C. was measured using an acoustic velocity measuring device (manufactured by Ultrasonic Engineering Co., Ltd., sing-around type acoustic velocity measuring device "UVM-2 type"), and the acoustic impedance was obtained from a product of the measured density and acoustic velocity.

(Ultrasonic Attenuation)

Regarding the obtained each sheet having a thickness of 3 mm, ultrasonic waves at 5 MHz were generated in water using an ultrasonic oscillator (manufactured by IWATSU TEST INSTRUMENTS CORPORATION, FUNCTION GENERATOR "FG-350"), and the magnitude of amplitude before and after ultrasonic waves transmits the sheet was measured using an ultrasonic wave receiver (manufactured by Matsushita Electric Industrial Co., Ltd., OSCILLOSCOPE "VP-5204A") under environment at a water temperature of 25° C.

The obtained results are collectively shown in the following Table 1.

TABLE 1

| Item | Unit | Example 1 | Example 2 | Example 3 | Comparative Example 1 | Comparative Example 2 | Comparative Example 3 | Comparative Example 4 |
|---|---|---|---|---|---|---|---|---|
| JIS hardness | [—] | 42 | 52 | 44 | 26 | 12 | 53 | 48 |
| Tensile rupture strength | [MPa] | 3.9 | 4.7 | 5.4 | 2.7 | 0.3 | 5.9 | 4.3 |
| Tensile rupture elongation | [%] | 1,100 | 310 | 460 | 230 | 450 | 1,310 | 1,230 |
| tear strength | [N/cm] | 20 | 25 | 28 | 16 | 1 | 85 | 31 |
| Acoustic impedance | [Mrayl] | 1.12 | 1.09 | 1.11 | 1.10 | 1.00 | 1.26 | 1.09 |
| Ultrasonic attenuation | [dB/mmMHz] | 0.45 | 0.55 | 0.48 | 0.43 | 0.15 | 0.84 | 0.74 |

As shown in Table 1, the silicone resins for an ultrasonic probe in Examples 1 to 3 show high resin hardness, tensile rupture strength, and tear strength while maintaining low ultrasonic attenuation which is less than 0.60 dB/mmMHz.

From these results, it was found that the composition for an ultrasonic probe of the present invention is useful for a medical member. Particularly, the composition can be favorably used in a material or the like of an acoustic matching layer which is provided in an acoustic lens of the ultrasound diagnostic apparatus or between a piezoelectric element and the acoustic lens and plays a role of matching acoustic impedance between the piezoelectric element and the acoustic lens.

What is claimed is:

1. A composition for an ultrasonic probe which contains a polyorganosiloxane mixture including at least three different polyorganosiloxanes, and which does not contain a carbon black, wherein the polyorganosiloxane mixture includes (A) a polyorganosiloxane having a vinyl group represented by the following General Formula (A), (B) a polyorganosiloxane having two or more Si—H groups in a molecular chain, and (C) a branched polyorganosiloxane represented by the following General Formula (C), and he content of the polyorganosiloxanes (A), (B), and (C) is respectively 10 to 99.4 parts by mass, 0.5 to 90 parts by mass, and 0.1 to 40 parts by mass, with respect to 100 parts by mass of the total mass of the polyorganosiloxanes (A), (B), and (C),

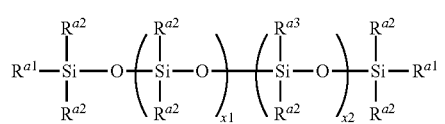

wherein in General Formula (A), $R^{a1}$ represents a vinyl group; $R^{a2}$ and $R^{a3}$ each independently represent an alkyl group, a cycloalkyl group, an alkenyl group, or an aryl group, x1 and x2 each independently represent an integer of 1 or more, a plurality of $R^{a2}$'s and a plurality of $R^{a3}$'s may be the same as or different from each other, and each group of $R^{a2}$ and $R^{a3}$ may be further substituted with a substituent,

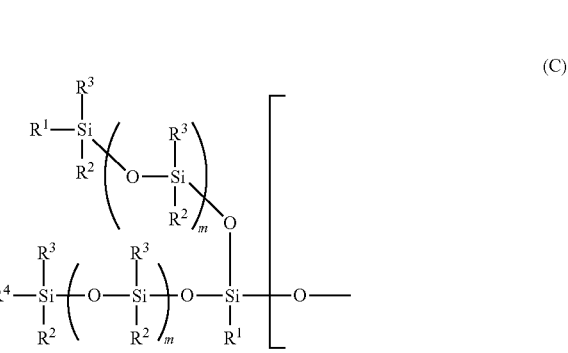

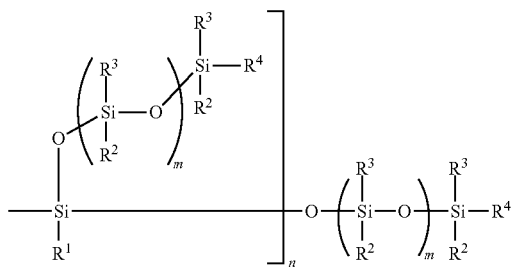

wherein in General Formula (C), $R^1$ to $R^4$ each independently represent an alkyl group, a cycloalkyl group, an alkenyl group, or an aryl group, m represents an integer of 1 or more and n represents 0 or an integer of 1 to 5, a plurality of $R^1$'s, a plurality of $R^2$'s, a plurality of $R^3$'s, a plurality of $R^4$'s, and a plurality of m's may be the same as or different from each other, each group of $R^1$ to $R^4$ may be further substituted with a substituent, and at least two of the plurality of $R^4$'s are alkenyl groups.

2. The composition for an ultrasonic probe according to claim 1, wherein (C) the branched polyorganosiloxane represented by General Formula (C) is a branched polyorganosiloxane represented by the following General Formula (C1),

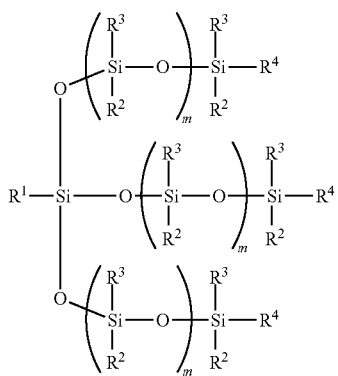

in General Formula (C1),
R$^1$ to R$^4$ each independently represent an alkyl group, a cycloalkyl group, an alkenyl group, or an aryl group, m represents an integer of 1 or more,
a plurality of R$^2$'s, a plurality of R$^3$'s, a plurality of R$^4$'s, and a plurality of m's may be the same as or different from each other, each group of R$^1$ to R$^4$ may be further substituted with a substituent, and
at least two of three R$^4$'s are alkenyl groups.

3. The composition for an ultrasonic probe according to claim 2,
wherein (B) the polyorganosiloxane having two or more Si—H groups in a molecular chain is a polyorganosiloxane represented by the following General Formula (B),

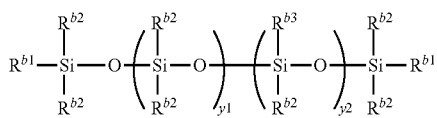

in General Formula (B),
R$^{b1}$ to R$^{b3}$ each independently represent a hydrogen atom, an alkyl group, a cycloalkyl group, an alkenyl group, an aryl group, or —O—Si(R$^{b5}$)$_2$(R$^{b4}$),
R$^{b4}$ and R$^{b5}$ each independently represent a hydrogen atom, an alkyl group, a cycloalkyl group, an alkenyl group, or an aryl group,
y1 and y2 each independently represent an integer of 1 or more,
a plurality of R$^{b1}$'s, a plurality of R$^{b2}$'s, a plurality of R$^{b3}$'s, a plurality of R$^{b4}$'s, and a plurality of R$^{b5}$'s may be the same as or different from each other,
each group of R$^{b1}$ to R$^{b5}$ may be further substituted with a substituent, and
the polyorganosiloxane has two or more Si—H groups in a molecular chain.

4. The composition for an ultrasonic probe according to claim 1,
wherein R$^1$ to R$^3$ are alkyl groups having 1 to 4 carbon atoms, R$^4$ is an alkyl group having 1 to 4 carbon atoms or a vinyl group, and at least two of the plurality of R$^4$'s are vinyl groups.

5. The composition for an ultrasonic probe according to claim 1,
wherein R$^1$ to R$^3$ are methyl groups and R$^4$ is a vinyl group.

6. The composition for an ultrasonic probe according to claim 1,
wherein (B) the polyorganosiloxane having two or more Si—H groups in a molecular chain is a polyorganosiloxane represented by the following General Formula (B),

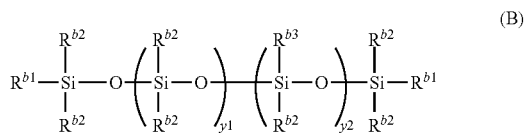

in General Formula (B),
R$^{b1}$ to R$^{b3}$ each independently represent a hydrogen atom, an alkyl group, a cycloalkyl group, an alkenyl group, an aryl group, or —O—Si(R$^{b5}$)$_2$(R$^{b4}$),
R$^{b4}$ and R$^{b5}$ each independently represent a hydrogen atom, an alkyl group, a cycloalkyl group, an alkenyl group, or an aryl group,
y1 and y2 each independently represent an integer of 1 or more,
a plurality of R$^{b1}$'s, a plurality of R$^{b2}$'s, a plurality of R$^{b3}$'s, a plurality of R$^{b4}$'s, and a plurality of R$^{b5}$'s may be the same as or different from each other,
each group of R$^{b1}$ to R$^{b5}$ may be further substituted with a substituent, and
the polyorganosiloxane has two or more Si—H groups in a molecular chain.

7. The composition for an ultrasonic probe according to claim 1,
further containing an inorganic filler,
wherein the content of the inorganic filler with respect to 100 parts by mass of the polyorganosiloxane mixture is 5 to 200 parts by mass.

8. The composition for an ultrasonic probe according to claim 1,
wherein the (A) polyorganosiloxane having a vinyl group includes at least a vinyl group-containing silicone resin, and
the content of the vinyl group-containing silicone resin with respect to 100 parts by mass of the total mass of the (A) component is 5 to 100 parts by mass.

9. The composition for an ultrasonic probe according to claim 1,
further containing a platinum or a platinum compound,
wherein the content of the platinum or the platinum compound with respect to 100 parts by mass of the polyorganosiloxane mixture is 0.01 to 5 parts by mass.

10. A silicone resin for an ultrasonic probe which is obtained by curing the composition for an ultrasonic probe according to claim 1.

* * * * *